United States Patent [19]

Pawlowski et al.

[11] Patent Number: 5,055,579

[45] Date of Patent: Oct. 8, 1991

[54] HETEROCYCLIC COMPOUNDS CONTAINING 4,6-BIS-TRICHLOROMETHYL-S-TRIAZIN-2-LY GROUPS

[75] Inventors: Georg Pawlowski, Wiesbaden; Heidrun Lutz, Mainz, both of Fed. Rep. of Germany

[73] Assignee: Hoechst Aktiengesellschaft, Frankfurt am Main, Fed. Rep. of Germany

[21] Appl. No.: 317,595

[22] Filed: Mar. 1, 1989

[30] Foreign Application Priority Data

Mar. 7, 1988 [DE] Fed. Rep. of Germany ....... 3807381

[51] Int. Cl.$^5$ ................. C07D 401/10; C07D 403/10; C07D 413/10; C07D 417/10
[52] U.S. Cl. ..................................... 544/216; 544/14; 544/32; 544/50; 544/89; 544/90; 544/96; 544/54; 544/1
[58] Field of Search .................. 544/216, 14, 32, 50, 544/89, 90, 96, 54, 1

[56] References Cited

U.S. PATENT DOCUMENTS

| | | | |
|---|---|---|---|
| 3,954,475 | 5/1976 | Bonham et al. | 96/67 |
| 4,189,323 | 2/1980 | Buhr | 430/281 |
| 4,212,970 | 7/1980 | Iwasaki | 542/455 |
| 4,232,106 | 11/1980 | Iwasaki et al. | 430/170 |
| 4,371,606 | 2/1983 | Dönges | 430/281 |
| 4,371,607 | 2/1983 | Dönges | 430/281 |
| 4,619,998 | 10/1986 | Buhr | 544/193.1 |
| 4,696,888 | 9/1987 | Buhr | 430/270 |
| 4,701,399 | 10/1987 | Nagano et al. | 430/179 |

FOREIGN PATENT DOCUMENTS

| | | |
|---|---|---|
| 135863 | 9/1984 | European Pat. Off. |
| 0135348 | 3/1985 | European Pat. Off. |
| WO81/02261 | 1/1981 | World Int. Prop. O. |

OTHER PUBLICATIONS

K. Wakabayashi et al., "Studies on S-Triazines. I. Co-trimerization of Trichloroacetonitrile with Other Nitriles", Bulletin of the Chemical Society of Japan, vol. 42, 1969, pp. 2924–2930.

*Primary Examiner*—John M. Ford
*Attorney, Agent, or Firm*—Foley & Lardner

[57] ABSTRACT

Compounds of general formula I are disclosed

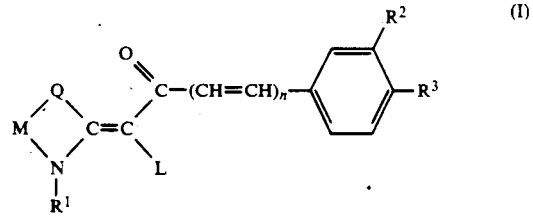

wherein
L denotes a hydrogen atom, an aryl radial or a substituent of the formula

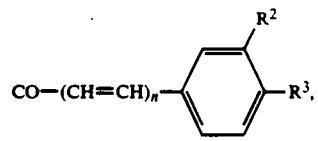

M denotes an alkylene radical or alkenylene radical or a 1,2-arylene radical,
Q denotes a sulfur, selenium or oxygen atom, a dialkylmethylene group, an alken 1,2-ylene radical, a 1,2-phenylene radical or an N-$R^1$ group,
denotes an alkyl, aralkyl, aryloxyalkyl or alkoxyalkyl radical,
$R^2$ and $R^3$ denote a hydrogen atom or a 4,6-bis-trichloromethyl-s-triazin-2-yl group, and
n is 0 or 1.

The compounds are suitable for use as photoinitiators in photosensitive systems that are induced to reaction by free radicals or acid cations. The compounds are characterized by high sensitivity in the visible spectral region.

8 Claims, No Drawings

HETEROCYCLIC COMPOUNDS CONTAINING 4,6-BIS-TRICHLOROMETHYL-S-TRIAZIN-2-LY GROUPS

BACKGROUND OF THE INVENTION

The present invention relates to heterocyclic aromatic compounds containing 4,6-bis-trichloromethyl-s-triazin-2-yl groups, to a process for their preparation and to a photosensitive composition containing these compounds.

It is known to employ aromatic or heterocyclic compounds containing trichloromethyl groups as initiators for various photochemical reactions.

DE-A 22 43 621 discloses s-triazines that are substituted by one or two trichloromethyl groups and one chromophoric group and are suitable as photoinitiators in photopolymerizable compositions and as acid donors in a mixture with acetals that can be split by acid. These compounds also include those that absorb light in the visible region of the electromagnetic spectrum and act as photoinitiators. Their sensitivity in this region is, however, insignificant.

Similar compounds, in which an at least binuclear aromatic radical as a chromphoric group is bonded directly to the triazine ring, are disclosed in DE-A 27 18 259 (=U.S. Pat. No. 4,189,323).

EP-A 137 452 describes similar 4,6-bis-trichloromethyl-s-triazines that have an optionally-substituted styryl group in the 2-position. The absorption peaks of these compounds are mostly in the near ultraviolet region.

DE-A 28 51 472 describes photosensitive compositions that contain 2-halogenomethyl-5-vinyl-1,3,4-oxadiazole derivatives as photoinitiators.

DE-A 30 21 590 and DE-A 30 21 599 disclose halogenoxazoles that are substituted by trichloromethylphenyl groups and are suitable as photoinitiators, like the above-mentioned compounds.

Moreover, EP-A 135 348 and EP-A 135 863 (corresponding to U.S. application Ser. No. 06/651,116) disclose 1-alkyl-2-carbonylmethylene-benzothiazoles and similar heterocyclic compounds, that carry a trichloromethylphenyl group on the carbonyl group. These compounds also have their maximum sensitivity in the near ultraviolet region.

The known photoinitiators have a number of disadvantages. The reaction conditions for preparing many of these compounds are fairly drastic so that the yield is relatively low and the formation of undesired by-products that are difficult to separate is favored (for example, DE-A 22 43 621, DE-A 27 18 259 or 28 51 472). With many known initiators, the inadequate sensitivity makes it necessary to combine different initiator systems with one another.

Basically, most of the above-described initiators can be used to prepare photosensitive compositions, the sensitivity of which is good in the near ultraviolet region, but inadequate in the visible region. Upon exposure to conventional lasers emitting visible light of relatively low energy, the initiating action of these lasers is either nonexistent or only very slight. Moreover, it has been found that precisely the most sensitive of the known initiators do not have a storage stability that meets the requirements of practical application in photosensitive compositions, in particular in contact with copper surfaces.

Since an increased use of lasers, in particular, of argon or krypton lasers that have an emission between 450 and 650 nm and are employed as recording lasers, has to be expected in the future, highly photosensitive initiators and compositions must be provided, that exhibit adequate sensitivities in these applications.

SUMMARY OF THE INVENTION

It is therefore an object of the present invention to provide novel photosensitive compounds that can be used in various photosensitive materials, that are relatively readily accessible and that offer a wide range of possible variations in practical use, thus being adaptable in an optimum manner to the requirements of each of the various fields of application.

It is, in particular, an object of the present invention to provide photosensitive compounds that have high sensitivities in the visible spectral region such that their activity is initiated even by weak light sources emitting visible light at wavelengths above 400 nm, in particular at 488 and 514 nm.

It is a further object of the present invention to provide photosensitive compounds that, when used in photosensitive compositions for reprography, for example in printing plates, show a clearly visible image contrast in the light-sensitive layer already after irradiation.

It is yet another object of the present invention to provide a photosensitive composition containing the novel initiators that has a high storage stability, irrespective of the material of the support on which the compositions are present.

These and other objects of the invention are achieved by compounds of general formula I

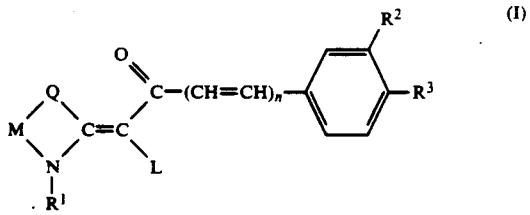

wherein
L denotes a hydrogen atom, an aryl radical or a substituent of the formula

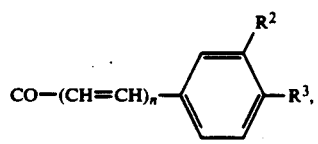

M denotes a substituted or unsubstituted alkylene radical or alkenylene radical or a 1,2-arylene radical,
Q denotes a sulfur, selenium or oxygen atom, a dialkylmethylene group, an alken-1,2-ylene radical, a 1,2-phenylene radical or an N-$R^1$ group,
with M +Q together forming 3 or 4 ring members,
$R^1$ denotes an alkyl, aralkyl, aryloxyalkyl or alkoxyalkyl radical,
$R^2$ and $R^3$ differ from one another and either denote a hydrogen atom or a 4,6-bis-trichloromethyl-s-triazin-2-yl group, and
n=0 or 1.

The invention also provides a photosensitive composition comprising a photosensitive organic compound (a) having at least one 4,6-bis-trichloromethyl-s-triazin-2-yl substituent and a compound (b) capable of reacting with the photoreaction product of compound (a) to form a product having a light absorption, tackiness or solubility in a developer, different from that of compound (b).

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

DETAILED DESCRIPTION OF THE PREFERRED EMBODIMENTS

The composition of the present invention comprises a compound according to formula I

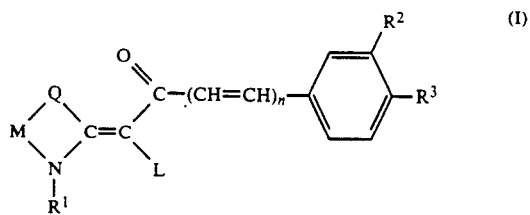

wherein

L denotes a hydrogen atom, an aryl radical or a substituent of the formula

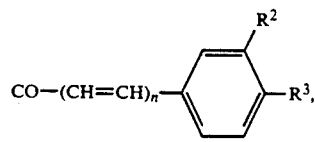

M denotes a substituted or unsubstituted alkylene radical or alkenylene radical or a 1,2-arylene radical, Q denotes a sulfur, selenium or oxygen atom, a dialkylmethylene group, an alken-1,2-ylene radical, a 1,2-phenylene radical or an N-$R^1$ group, with M +Q together forming 3 or 4 ring members, $R^1$ denotes an alkyl, aralkyl, aryloxyalkyl or alkoxyalkyl radical, $R^2$ and $R^3$ differ from one another and either denote a hydrogen atom or a 4,6-bis-trichloromethyl-s-triazin-2-yl group, and n is 0 or 1.

Under the action of actinic radiation, the compounds according to the present invention form free radicals that are capable of initiating chemical reactions, in particular polymerizations initiated by free radicals. Upon irradiation, the compounds also form hydrogen halide, by means of which acid-catalyzed reactions, for example the cleavage of acetal bonds, or formation of salts, for example color changes of indicator dyes, can be effected.

In formula I, L is preferably a hydrogen atom; when L is an aryl radical it is preferably a phenyl radical which can be substituted. M is preferably a 1,2-phenylene radical that is preferably unsubstituted, but can be substituted, for example, by halogen atoms or carboxyl, sulfonic acid, nitro, cyano, carbonyl, alkyl, aryl, alkoxy, trifluoromethyl or alkoxycarbonylalkyl groups. M can also be a heterocyclic aromatic radical, for example, a pyridylene radical. When M is a polynuclear arylene radical, it can contain 2 or 3, but preferably 2 benzene nuclei. M can also be a 1,2- or 1,3-alkenylene radical which can be substituted, for example, by halogen atoms or carboxyl, carbonyl, alkoxy, alkyl or aryl groups. Moreover, M can be a 1,1-, 1,2,- or 1,3-alkylene radical that may also carry substituents of the same type.

Q is preferably a sulfur or selenium atom, an $NR^1$ group or a dialkylmethylene group having 3 to 13, preferably 3 to 7, and especially 3 carbon atoms. Q can also be an oxygen atom, a 1,2-alkenylene group, a 1,2-phenylene group or a carbonyl or thiocarbonyl group. If Q is a dialkylmethylene group, the alkyl groups can be linked to one another with the formation of a 5-membered or 6-membered ring. If Q is a 1,2-alkenylene group, Q can be substituted, among others, by one or two alkyl or aryl radicals, chlorine atoms, alkoxy groups or alkoxycarbonyl groups. If Q is a 1,2-phenylene radical, the latter can contain, for example, chlorine atoms or alkoxy or alkoxy carbonyl groups as substituents. Preferably, Q is S, Se or $C(CH_3)_2$, in particular as a constituent of a 5-membered ring.

When $R^1$ is an alkyl or alkoxyalkyl radical, it can, in general, comprise 1 to 10, preferably 1 to 6 carbon atoms. The radical can be straight-chain or branched, or it can be cyclized to give a cycloaliphatic radical, for example, a cyclohexyl radical. Examples of aralkyl radicals include benzyl, chlorobenzyl, tolylmethyl and phenethyl radicals. As an aryloxyalkyl radical a phenoxyethyl radical can, for example, be used. Particularly preferably, $R^1$ is an alkyl radical having 1 to 6 carbon atoms.

In general, compounds with n=1 are preferred.

The compounds according to the present invention can advantageously be prepared analogously to know processes [for example, A Mistr. V. Laznicka and M. Vavra, Coll. Czech. Chem. Commun. 36, 150 (1971)] from a methylene compound of formula II or the corresponding iminium salt of formula III and a carboxylic acid halide of formula IV:

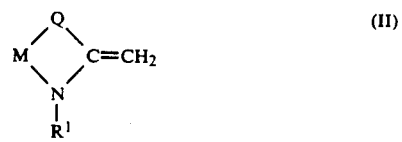

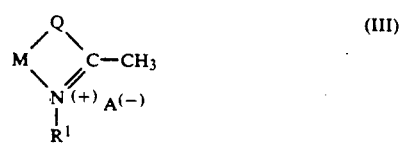

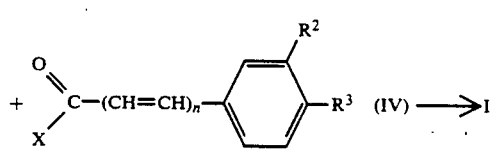

wherein A is an inorganic anion, preferably a halide anion, tetrafluoborate anion or perchlorate anion, or an organic anion, preferably a sulfonate anion or alkylsulfate anion, X is a halogen atom and the remaining symbols are as defined above.

The reaction preferably takes place under the action of nitrogen bases, for example, triethylamine, dimethylbenzylamine, diethylbenzylamine, N-ethyldicyclohexylamine, N-ethylpiperidine, N-methylpiperidine, N-methylmorpholine, N-ethylmorpholine, N-ethylpyrrolidone, 1,8-diazabicyclo-[5,4,0]undec-7-ene, 1,4-diazabicyclo[2,2,2]octane or pyridine; the base itself may be used as the solvent or an inert organic solvent is added. The solvents added include, for example, benzene, toluene, dimethylformamide, tetrahydrofuran, diethyl ether, diisopropyl ether and methylene chloride. The reaction is advantageously carried out at temperatures between about 0° and 100° C., the quantity of the carboxylic acid halide generally being between about 1 and 4 moles per mole of II or III. For the preparation of products with L=H preferably between about 1 and 1.5 moles per mole of II or III are used, and for the preparation of disubstituted products between about 2 and 3 moles per mole of II or III are used.

The acid halides of formula IV can be prepared by cotrimerizing trichloroacetonitrile with 3- or 4-cyanobenzoyl or cinnamoyl chloride under the action of HCl gas, in the presence of a Lewis acid. Preferably, however, the 3-or 4-(4,6-bis-trichloromethyl-s-triazin-2-yl)-benzoic or cinnamic acid is first prepared by a corresponding cotrimerization with 3- or 4-cyanobenzoic or cinnamic acid methylester, transesterification of the esters obtained with trichloroacetic acid, in the presence of a strong mineral acid and distillation of the trichloroacetic acid methylester formed and the acid obtained is converted, e.g., with thionyl chloride, into the acid chloride.

The preparation of these compounds is described in detail in application Ser. No. 07/317,562 (corresponding to German Application P 38 07 378.1), filed concurrently herewith. The contents of this application are hereby incorporated by reference.

Some of the compounds corresponding to formulae II and III are commercially available, others are readily accessible according to known methods.

The compounds according to the invention are suitable as photoinitiators for photopolymerizable layers that contain polymerizable compounds, initiators and optionally binders as the essential constituents.

The polymerizable compounds employed in the photosensitive compositions according to the present invention contain at least one ethylenic double bond and can be present in the form of monomers, oligomers, polymers or mixtures of these components. Examples of suitable compounds are optionally polyunsaturated carboxylic acids and the salts thereof, acid derivatives such as esters or amides, derivatives obtained from carbonic acid, for example, urethanes, sulfonyl urethanes or phosphinyl urethanes or the corresponding urea compounds, unsaturated ethers and unsaturated derivatives obtainable from epoxides.

Examples of carboxylic acids are acrylic acid, methacrylic acid, itaconic acid, crotonic acid, isocrotonic acid, and maleic acid. Examples of salts of carboxylic acids are the sodium and potassium salts of the aforementioned carboxylic acids.

Suitable esters of unsaturated carboxylic acids with optionally polyhydric alcohols include the esters of acrylic and methacrylic acids, such as ethylene glycol di(meth)acrylate, triethylene glycol di(meth)acrylate, 1,3-butanediol di(meth)acrylate, tetramethylenediol di(meth)acrylate, propylene glycol di(meth)acrylate, trimethylolpropane tri(meth)acrylate, trimethylolethane tri(meth)acrylate, 1,4-cyclohexanediol di(meth)acrylate, tetraethyleneglycol di(meth)acrylate, pentaerythritol di(meth)acrylate, pentaerythritol tri(meth)acrylate, pentaerythritol tetra(meth)acrylate, dipentaerythritol di(meth)acrylate, sorbitol tri(meth)acrylate, sorbitol tetra(meth)acrylate, sorbitol penta(meth)acrylate, sorbitol hexa(meth)acrylate, and polyester(meth)acrylate oligomers, 2,2-bis-[p-(3-(meth)acryloyloxy-2-hydroxypropoxy)-phenyl]-propane and 2,2-bis[(meth)acryloyloxy-ethoxy-phenyl]-propane; esters of itaconic acid, such as ethylene glycol diitaconate, propylene glycol diitaconate, 1,3-butanediol diitaconate, 1,4-butanediol diitaconate, tetramethylenediol diitaconate, pentaerythritol diitaconate and sorbitol tetraitaconate; esters of crotonic acid, such as ethylene glycol dicrotonate, tetramethylenediol dicrotonate, pentaerythritol dicrotonate and sorbitol tetracrotonate; esters of isocrotonic acid, such as ethylene glycol diisocrotonate, pentaerythritol diisocrotonate and sorbitol tetraisocrotonate; and esters of maleic acid, such as ethylene glycol dimaleinate, triethyleneglycol dimaleinate, pentaerythritol dimaleinate and sorbitol tetramaleinate. These esters can be used individually or as mixtures.

Amides of unsaturated carboxylic acids with optionally polyvalent amines can be used comprising acrylamides and methacrylamides, for example, methylene-bis-(meth)acrylamide, 1,6-hexamethylene-bis-(meth)acrylamide, diethylenetriamine-tris(meth)acrylamide and xylylene-bis-(meth)acrylamide.

Further preferred polymerizable compounds containing at least one ethylenically unsaturated bond comprise vinyl urethane compounds having at least two polymerizable vinyl groups in the molecule, obtained by the addition reaction of a hydroxyalkyl(meth)acrylate, for example, hydroxyethylmethacrylate or 2-hydroxypropylacrylate, with an isocyanate having at least two isocyanate groups in the molecule, or those obtained by addition reaction from an isocyanatoalkyl(meth)acrylate, for example, 2-isocyanatoethylmethacrylate, and a polyhydric alcohol that may contain nitrogen atoms.

Of the above-specified compounds, the acrylic and methacrylic esters of polyhydric alcohols and the reaction products of diisocyanates with partial esters of polyhydric unsaturated alcohols, and the reaction products of hydroxyalkyl(meth)acrylates with polyisocyanates and isocyanatoalkyl(meth)acrylates with polyalcohols represent particularly preferred polymerizable components. Examples of the last-mentioned monomers are described in DE-A 20 64 079, DE-A 23 61 041 and DE-A 28 22 190. The amount of monomers in the layer is, in general, about 10% to 80% by weight, preferably about 20% to 60% by weight, based on the amount of non-volatile constituents.

When the photoinitiators according to the present invention are used in photopolymerizable compositions, the latter may also contain a binder. The binder must be compatible with the ethylenically unsaturated polymerizable compound and with the photoinitiator of the invention. After the imagewise exposure it must be possible to process the photosensitive layer by washing out or peel apart. Moreover, the binder should impart sufficient toughness, strength, abrasion resistance and flexibility to the photosensitive layer. The binder usually comprises a linear organic polymer.

Binders that may be used include, for example, chlorinated polyethylene, chlorinated polypropylene, polyalkyl(meth)acrylates, in which the alkyl group is, for example, methyl, ethyl, n-butyl, i-butyl, n-hexyl or 2-ethylhexyl, copolymers of the alkyl(meth)acrylates mentioned with at least one monomer, such as acrylonitrile, vinyl chloride, vinylidene chloride, styrene or butadiene; polyvinyl chloride, vinyl chloride/acrylonitrile copolymers, polyvinylidene chloride, vinylidene chloride/acrylonitrile copolymers, polyvinyl acetate, polyvinyl alcohol, polyacrylonitrile, acrylonitrile/styrene copolymers, acrylonitrile/butadiene/styrene copolymers, polystyrene, polymethylstyrene, polyamides (e.g. Nylon-6), polyurethanes, methyl cellulose, ethyl cellulose, acetyl cellulose, polyvinylformal, and polyvinylbutyral.

Binders that are insoluble in water and soluble in organic solvents and soluble or at least swellable in aqueous-alkaline solutions are particularly suitable.

Especially preferred are binders containing carboxyl groups, for example, copolymers of (meth)acrylic acid and/or the unsaturated homologs thereof, such as crotonic acid, copolymers of maleic anhydride or the half-esters thereof, reaction products of polymers containing hydroxyl groups with dicarboxylic acid anhydrides and mixtures thereof.

Other suitable binders include reaction products of polymers carrying groups which contain acidic hydrogen, all or some of which have been reacted with activated isocyanates, for example, reaction products of polymers containing hydroxyl groups with aliphatic or aromatic sulfonyl isocyanates or phosphinic acid isocyanates.

The following are also suitable: polymers containing hydroxyl groups, for example, copolymers of hydroxyalkyl(meth)acrylates, copolymers of allyl alcohol, copolymers of vinyl alcohol, polyurethanes or polyesters, as well as epoxy resins, provided these contain a sufficient number of free OH groups or are modified so that they are soluble in aqueousalkaline solution, or polymers containing phenolic hydroxyl groups, for example, condensation products of condensible carbonyl compounds, in particular, formaldehyde, acetaldehyde or acetone, with phenols; or copolymers of hydroxystyrenes. It is also possible to use copolymers of (meth)acrylic acid amide with alkyl(meth)acrylates.

The above-described polymers are, in particular, suitable when they have a molecular weight between 500 and 200,000 or above, preferably 1,000 to 100,000, and either have acid numbers between 10 and 250, preferably 20 to 200, or hydroxyl numbers between 50 and 750, preferably 100 to 500.

The preferred alkali-soluble binders include copolymers of (meth)acrylic acid with alkyl(meth)acrylates, (meth)acrylic acid nitrile or the like; copolymers of crotonic acid with alkyl(meth)acrylates, (meth)acrylic acid nitrile or the like; copolymers of vinyl acetic acid with alkyl(meth)acrylates; copolymers of maleic anhydride with optionally substituted styrenes, unsaturated hydrocarbons, unsaturated ethers or esters; esterification products of the copolymers of maleic anhydride; esterification products of polymers containing hydroxyl groups with anhydrides of dicarboxylic acids or polycarboxylic acids, copolymers of hydroxyalkyl(meth)acrylates with alkyl(meth)acrylates, (meth)acrylic acid nitrile and the like; copolymers of allyl alcohol with optionally substituted styrenes; copolymers of vinyl alcohol with alkyl(meth)acrylates or other unsaturated compounds that are capable of polymerizing; polyurethanes, provided they have a sufficient number of free OH groups; epoxy resins; polyesters; partially-saponified vinyl acetate copolymers; polyvinyl acetals having free OH groups; copolymers of hydroxystyrenes with alkyl(meth)acrylates or the like; and phenol/formaldehyde resins, e.g. novolaks.

The amount of binder in the photosensitive layer comprises, in general, about 20% to 90% by weight, preferably about 40% to 80% by weight.

The photoinitiators according to the present invention are added to layers of this type in amounts ranging between about 0.1% and 15.0% by weight, preferably between about 0.2% to 5% by weight.

Depending on the intended use and depending on the desired properties, the photopolymerizable compositions can comprise various substances as additives, e.g., inhibitors to prevent thermal polymerization, hydrogen donors, substances which regulate the spectral sensitivity, dyes, colored and colorless pigments, color precursors, indicators and plasticizers.

Inhibitors that can be used comprise, for example, hydroquinone, p-methoxyphenol, di-t-butyl-p-cresol, pyrogallol, t-butyl-pyrocatechol, benzoquinone, cuprous chloride, phenothiazine, chloranil, naphthylamine, naphthol, nitrobenzene, and dinitrobenzene.

Suitable dyes or pigments include, for example, methylene blue, crystal violet, Rhodamine B, fuchsin, aurin, azo dyes, anthraquinone dyes, titanium dioxide, carbon black, ferric oxide, phthalocyanine pigments, or azo pigments; care has to be taken, however, that the absorption of the dye used is not too high in the initiation range of the photoinitiator.

Examples of plasticizers include phthalic acid esters, glycol esters, phosphoric acid esters, or aliphatic dicarboxylic acid esters.

The composition can also contain a sensitizer and/or an additional photoinitiator, selected to increase the photopolymerization rate, when they are used together with the photoinitiator of general formula I. Sensitizers that can be used include benzoin, benzoin alkylether, 9-fluorenone, 2-bromo-9-anthrone, 2-ethyl-9-anthrone, 9,10-anthraquinone, substituted anthraquinones, xanthone, substituted xanthones, thioxanthone, benzil, dibenzalacetone, substituted chalcones, benzophenone or benzanthrone, eosin or fluorescein derivatives, acridines, pyronines or similar substances.

Suitable co-initiators are, in particular, photoinitiators containing trichloromethyl groups, whose absorption peaks are clearly below the absorption peaks of the photoinitiators according to the present invention. The oxadiazole derivatives described in the simultaneously-filed application Ser. No. 07/317,560 (corresponding to German Application No. P 38 07 380.3), are, for example, particularly suitable. The contents of this copending application are hereby incorporated by reference. By means of these measures the spectral sensitivity of the photosensitive composition can be extended over a large wavelength region.

The photopolymerizable composition can be used for various applications, for example, for the production of safety glass, as surface coatings which are cured by light or corpuscular radiation, for example electron beams, in the dental field and especially as a photosensitive copying material in the reproduction field. Possible applications of the latter include copying layers for the photomechanical production of printing forms for letterpress printing, flexographic printing, planographic printing, gravure printing and screen printing or relief copies, for examples, for the preparation of texts in Braille, of single copies, tanned images, pigment images and the like. Moreover, the compositions can be used for the photomechanical production of etch resists, for example, for making name tags, printed circuits and for chemical milling.

The commercial utilization of the composition for the applications mentioned can be in the form of a liquid solution or dispersion, for example, as a photoresist solution, applied by the user to an individual support, for example, for chemical milling and for the production of printed circuits, screenprinting stencils and the like. The composition can also be present as a solid photosensitive layer on a suitable support in the form of a precoated storable photosensitive copying material, for example, for the preparation of printing forms. It is likewise suitable for the preparation of dry resists.

In general, it is advantageous to protect the compositions from the influence of atmospheric oxygen during the photopolymerization. When the composition is used in the form of thin copying layers, it is advisable to apply a suitable covering film having low oxygen permeability. This film can be self-supporting and can be peeled off before the copying layer is developed. For example, polyester films are suitable for this purpose. The covering film can also comprise a material that is soluble in the developer fluid or can at least be removed from the unhardened areas during developing. Examples of materials suitable for this purpose are waxes, polyamides, polyvinyl alcohol, polyphosphates, sugars and the like.

Examples of suitable supports for the copying materials produced with the composition according to the present invention are aluminum, steel, zinc, copper and plastic films, for example, of polyethylene terephthalate or cellulose acetate, and screen-printing supports such as gauze polyamide 6.

Moreover, the compounds according to the invention can be used in radiation-sensitive compositions in which a change in properties is initiated by acid catalysts formed during the photolysis of the initiator. For instance, the cationic polymerization of systems which contain vinyl ethers, N-vinyl compounds, such as N-vinylcarbazole, or special acid-cleavable lactones, may be mentioned here, and free-radical processes can also participate in some of these reactions. Further acid-curable compositions include aminoplasts, such as urea/-formaldehyde resins, melamine/formaldehyde resins and other N-methylol compounds as well as phenol/-formaldehyde resins. Even though the hardening of epoxy resins generally takes place by means of Lewis acids or acids, the anions of which are less nucleophilic than chloride, that is to say the anion of the hydrohalic acid that is formed during the photolysis of the novel compounds, layers comprising epoxy resins and novolaks are, nevertheless, fully cured on exposure to light in the presence of the compounds according to the invention.

A further advantageous property of the novel compounds is their ability to cause color changes in dyed systems during photolysis, namely to induce color formation from color precursors, for example, leuco compounds, or to effect bathochromic color shifts and deepening in compositions which contain cyanine, merocyanine or styryl dye bases. Moreover, for example, in the compositions described in DE-A 15 72 080, containing a dye base, N-vinylcarbazole and a halohydrocarbon, the halogen compound tetrabromo-methane can be replaced by a compound according to the present invention in a quantity that is a fraction of the quantity of the former. Color changes are also desired in industry, for example, in the production of printing forms, so that the result of copying can be assessed after exposure even before developing.

The present compounds can be used advantageously in place of the acid donors mentioned in DE-A 23 31 377 and 26 41 100.

A particularly preferred field of application for the compounds according to the invention is in compositions that, in addition to the latter, contain a compound with at least one C-O-C grouping, that can be split by acid, as an essential component. The following may be mentioned as preferred compounds that can be split by acid:

A) those having at least one orthocarboxylate and/or carboxamide acetal grouping, it also being possible for the compounds to have a polymeric character and for the groupings to be present as linking elements in the main chain or as lateral substituents,
B) polymer or oligomer compounds with recurring acetal and/or ketal groupings or monomer acetals or ketals,
C) polymer compounds with recurring units of activated esters of carbonic acid.
D) compounds containing at least one enol ether or N-acyliminocarbonate group,
E) cyclic acetals or ketals of $\beta$-ketoesters or -amides,
F) compounds containing silyl ether groups,
G) compounds containing silylenol ether groups,
H) monoacetals or monoketals whose aldehyde or ketone components have a solubility in the developer between 0.1 and 100 g/l,
I) ethers based on the tertiary alcohols, and
K) carboxylates and carbonates of tertiary, allylic or benzylic alcohols.

Type A compounds, that can be split by acid, as components of radiation-sensitive compositions are described in detail in DE-A 26 10 842 or 29 28 636; compositions containing Type B compounds are the subject of DE-C 27 18 254, and compositions containing Type C compounds are described in EP-A 102 450.

As compounds that can be split by acid, the aryl alkyl acetals and aminals of DE-C 23 06 248, that are likewise degraded by the photolysis products of the compounds according to the present invention, may also be mentioned as examples.

Compounds of Type D are mentioned in EP-A 0 006 626 and 0 006 627; compounds of Type E are presented in EP-A 0 202 196; compound belonging to F are presented in DE-A 35 44 165 and DE-A 36 01 264; compounds of Type G are found in U.S. Patent application Ser. No. 243,819, filed Sept. 13, 1988 and compounds of Type G are discussed in U.S. Patent applications Ser. Nos. 243,818 and 243,792, likewise filed Sept. 13, 1988. Compounds of Type H are described, for example, in U.S. Pat. No. 4,603,101, and compounds of Type I for example, in U.S. Pat. No. 4,491,628 and by J. M. Fréchet et al., *J. Imaging Sci.*, 30: 59-64 (1986). The contents of these references are hereby incorporated by reference.

Those compositions in which molecules are converted into smaller molecules directly or indirectly by the action of actinic radiation have, in general, an increased solubility, tackiness or volatility in the irradiated areas. These portions can be removed by suitable measures, for example by dissolution with a developer fluid. In copying materials these are called positive-working systems.

The novolak condensation resins, proven in many positive copying materials, have also proved to be particularly useful and advantageous as additives when the compounds according to the invention are used in compositions with compounds that can be split by acid. The resins promote the strong differentiation between the exposed and unexposed layer portions on developing, in particular, the more highly condensed resins with substituted phenols as the formaldehyde condensation partners. The nature and quantity of the novolak resins can vary depending on the intended purpose; amounts of novolak between about 30% and 90% by weight, particularly between about 55% and 85% by weight, based on total solids, are preferred.

In addition, numerous other resins can also be included, preferably vinyl polymers, such as polyvinyl acetates, polyacrylates, polyvinyl ethers and polyvinylpyrrolidones, that in turn can have been modified by comonomers. The most advantageous proportion of these resins depends on the requirements in the particular application and the influence on the developing conditions. In general, the proportion is not more than about 20% of the novolak. For special requirements, such as flexibility, adhesion and gloss and the like, the photosensitive composition can also contain small quantities of substances such as polyglycols, cellulose derivatives such as ethyl cellulose, wetting agents, dyes and finely-divided pigments as well as ultraviolet absorbers, when required. Developing is preferably carried out with the aqueous-alkaline developers that are common in industry and that may contain small amounts of organic solvents, or with organic solvents.

The supports already listed in connection with the photopolymerizable compositions can also be used for positive-working copying materials, further suitable supports are the silicon, silicon dioxide, and gallium arsenide surfaces conventional in microelectronics.

The quantity of the compounds according to the invention, used as the photoinitiator in a positive-working composition can vary widely depending on the substance and layer. Fairly advantageous results are obtained with quantities between about 0.1% and 10%, preferably between about 0.2% to 5%, based on total solids. For layers having thicknesses exceeding 10 $\mu$m it is advisable to use relatively small quantities of acid donor.

Electromagnetic radiation of wavelengths up to about 700 nm is in principle suitable for exposure. The preferred wavelength range extends from about 300 to 600 nm. The compositions of the present invention exhibit maximum sensitivity in the range between 350 and 550 nm.

The wide variety of the compounds according to the invention, the absorption peaks of which are often to be found in the visible part of the spectrum and the spectral sensitivity of which often extends beyond 600 nm, makes it possible to match the photoinitiator in an optimum manner to the light source used. Light sources that may be used include fluorescent tubes, pulsed xenon lamps, metal halidedoped mercury vapor high-pressure lamps and carbon arc lamps.

Moreover, with the photosensitive compositions according to the present invention, exposure in conventional projection and enlargement apparatus under the light of metal filament lamps and contact exposure with ordinary incandescent bulbs can advantageously be performed. The exposure can also be made with the coherent light of a laser. Lasers suitable for the purposes of the present invention include, for example, argon ion lasers, by means of which a practically appropriate utilization of the emission at 488 and 514 nm is ensured, krypton ion lasers, dye lasers, helium/cadmium lasers or helium/neon lasers, by means of which the lines between 400 and 650 nm can be used particularly advantageously. The laser beam is, in general, monitored by means of a predetermined programmed line and/or screen movement.

Irradiation with electron beams is a further possibility. Electron beams can thoroughly decompose and crosslink compositions comprising one of the compounds according to the invention and a compound that can be split by acid, and also many other organic materials, so that a negative image is produced when the non-irradiated portions are removed by solvents or exposure without an original, and developing.

At a lower intensity and/or a higher writing speed of the electron beam, however, the electron beam effects a differentiation in the direction of higher solubility, that is, the irradiated layer portions can be removed by the developer. The most advantageous conditions can readily be established by preliminary experiments.

The radiation-sensitive compositions comprising the compounds according to the invention are preferably used in the production of printing forms, particularly offset printing forms, letterpress printing forms, flexographic printing forms, halftone gravure printing forms and screenprinting forms, in photoresist solutions and in dry resists.

Owing to the properties of the compounds according to the present invention photosensitive recording materials are obtained having numerous advantages compared with the prior art. Among these advantages is the capability of being exposed to light sources emitting light in the visible is especially important, sensitivities of the photosensitive recording material being obtained that are at least equal to the sensitivities of known compounds that are only sensitive in the near ultraviolet region. As a result, speedy exposure in accordance with practical requirements is insured using low-energy lasers emitting light in the visible region. The high susceptibility to atmospheric oxygen frequently observed in photosensitive compositions that can be activated at longer wavelengths occurs only to a minor degree, when the photoinitiators according to the present invention are employed. In addition, the photosensitive layers have an exceptionally high storage stability, resulting from the high chemical and thermal stability of the photoinitiators of the invention. This means that stocks can be maintained and the solutions or photosensitive layers can be stored for a prolonged period of time. Another important advantage is that the photosensitive compositions, in which the photoinitiators or acid donors, respectively, of the present invention are used, undergo hardly any catalytically-initiated dark reactions on critical surfaces, e.g., copper surfaces. This alone represents an improvement over the prior art.

Although the photosensitive compositions are very sensitive to visible light and must therefore be handled under appropriate conditions, in the extreme case under red light, the compounds of the present invention are extraordinarily stable to light and heat when in the crystalline state. They can therefore be prepared and handled without any greater expense under virtually normal production conditions and are stable for a long time in this state, so that stocks of these compounds can be maintained that are appropriate for practical purposes.

The examples that follow serve to explain the invention in more detail; the preparation of various compounds according to the invention is described first, and this is followed by the use of some of these compounds in radiation-sensitive compositions.

In the examples, parts by weight (pbw) and parts by volume (pbv) have the same relationship as the g and the ml. Unless otherwise stated, percentage data and quantitative data are to be understood as weight units.

PREPARATION EXAMPLE 1 a) 2,3-dimethyl-benzothiazolium-p-toluenesulfonate

2-Methylbenzothiazole (74.6 pbw) and methyl toluenesulfonate (93.1 pbw) are mixed with one another and heated with stirring. At about 120° C. an exothermic reaction starts, in which the temperature of the mixture rises to 180° C. The solution is kept at this temperature for 10 minutes and then cautiously poured into 1000 pbw of acetone. The suspension obtained is stirred for one hour. The precipitate is removed by filtration with suction and washed with acetone. The powder obtained is dried in vacuo over phosphorus pentoxide.

Yield: 147.2 pbw =87.8% of theory.

b) 2-[4-(4,6-bis-trichloromethyl-s-triazin-2-yl) benzoylmethylene]-3-methylbenzothiazoline (compound 1)

2,3-Dimethylbenzothiazolium-p-toluenesulfonate (13.4 pbw) and 4-(4,6-bis-trichloromethyl-s-triazin2-yl)-benzoylchloride (22.7 pbw) are successively suspended or dissolved, respectively, in 150 pbw of toluene. The mixture is cooled to 15° C. and with the exclusion of moisture 13.1 pbw of triethylamine are added dropwise at this temperature. The mixture discolors towards dark brown and is stirred for 3 hours at room temperature. The precipitate formed is removed by filtration with suction and washed with cold toluene. The residue is digested in 200 pbw of methanol and stirred for about 60 minutes, again filtered and dried.

The product is recrystallized from 2-methoxyethanol, giving orange-colored crystals.

Yield: 22 pbw 96.9% of theory, MP 243° C. (decomposition)

$C_{21}H_{12}Cl_6N_4OS$ (581.1): calc.: C 43.40, H 2.08, N 9.64, S 5.52, Cl 36.60; found: C 43.4, H 2.0, N. 9.6, S 5.7, Cl 35.9.

UV ($CH_2Cl_2$): λ max=426 nm.

PREPARATION EXAMPLE 2 a) 3-ethyl-2-methyl-benzothiazolium-p-toluenesulfonate

2-Methylbenzothiazole (300 pbw) and ethyl p-toluenesulfonate (440 pbw) are heated with stirring to 150° C., the temperature rising to about 200° C. due to the exothermic reaction. After 10 minutes, the mixture is poured into 2000 pbw of acetone, and the product that precipitates is removed by filtration with suction, washed with acetone and dried over phosphorous pentoxide.

Yield 730 pbw =98% of theory.

b) 2-(bis-[4-(4,6-bis-trichloromethyl-s-triazin-2-yl)benzoyl]-methylene)-3-ethylbenzothiazoline (compound 38)

4-(4,6-Bis-trichloromethyl-s-triazin-2-yl)benzoylchloride (22.7 pbw) are added dropwise to 7 pbw of 2-methyl-3-ethyl-benzothiazolium-p-toluenesulfonate in 30 pbw of dry pyridine at 8° C. The mixture is refluxed with stirring and allowed to cool after 150 minutes. The pyridine is removed by distillation in vacuo and the residue is admixed with 100 pbw of methanol. The mixture is digested for 1 hour, the residue is removed by filtration and washed with methanol. After drying, the product is recrystallized from acetonitrile, giving yellow crystals.

Yield: 11.3 pbw =56% of theory, MP 146°–147° C.

$C_{34}H_{17}Cl_{12}N_7O_2S$ (1013.0): calc.: C 40.31, H 1.69, N 9.6, S 3.20, Cl 42.00; found: C 40.6, H 1.7, N 9.8, S 3.0, Cl 42.5.

UV ($CH_2Cl_2$): λ max=385 nm.

PREPARATION EXAMPLE 3

2-[4-(4,6-bis-trichloromethyl-s-triazin-2-yl)benzoylmethylene]-1,3,3-trimethyl-indoline (compound 29)

4-(4,6-Bis-trichloromethyl-s-triazin-2-yl)benzoylchloride (15.4 pbw) are added dropwise with stirring at 10° C. to 5.2 pbw of 1,3,3-trimethyl-2-methylene-indoline and 10.6 pbw of triethylamine in 140 pbw of anhydrous toluene. The mixture is stirred for 3 hours at room temperature. It is then admixed with 100 pbw of water and 200 pbw of ether and extracted by shaking. The dried organic phase is concentrated. The residue is recrystallized from 2-methoxy-ethanol, giving red-orange crystals.

Yield: 10.2 pbw 57% of theory, MP 215° C. (decomposition).

$C_{24}H_{18}Cl_6N_4O$ (591.2): calc. C 48.76, H 3.07, N 9.48, Cl 36.00; found: C 48.5, H 3.0 , N 9.4, Cl 36.6.

UV ($CH_2Cl_2$): λ max=422 nm.

PREPARATION EXAMPLE 4

2-[3-(4,6-bis-trichloromethyl-s-triazin-2-yl)benzoylmethylene]-3-ethyl-benzothiazoline (compound 25)

3-Ethyl-2-methyl-benzothiazolium-p-toluenesulfonate (5.0 pbw) and 3-(4,6-bis-trichloromethyl-s-triazin-2-yl) benzoylchloride (7.4 pbw) are successively suspended or dissolved, respectively, in 50 pbw of toluene. The mixture is cooled to 15° C. and, at this temperature, 6.0 pbw of triethylamine are added dropwise with the exclusion of moisture. The mixture discolors towards dark brown and is stirred for 3 hours at room temperature. The precipitate that forms is removed by filtration with suction and washed with cold toluene. The residue is digested in 200 pbw of methanol and stirred for about 60 minutes, filtered again and dried. The product is recrystallized from 2-methoxy-ethanol, giving orange-colored crystals.

Yield: 6.2 pbw 72.8% of theory, MP 191.5°–193.0° C. (decomposition).

$C_{22}H_{14}Cl_6N_4OS$ (595.1): calc. C 44.40, H 2.37 , N 9.41, S 5.39, Cl 35.74; found: C 44.4, H 2.3, N 9.3, S 5.6, Cl 35.4.

UV ($CH_2Cl_2$): λ max=385 nm.

PREPARATION EXAMPLE 5 a) 1,2-dimethyl-quinolinium-p-toluenesulfonate

2-Methyl-quinoline (71.5 pbw) and methyl-p-toluenesulfonate (102.3 pbw) are heated for about 10 minutes at 100° C. An exothermic reaction sets in, in which the mixture is heated to 180.C. After another 10 minutes the mixture is poured onto acetone, filtered with suction, washed with acetone and dried.

Yield: 150 pbw =92% of theory.

b)

2-[4-(4,6-bis-trichloromethyl-s-triazin-2-yl)benzoylmethylene]-1-methyl-1,2-dihydroquinoline (compound 39)

Triethylamine (17.4 pbw) are added dropwise at 15° C. to 14.1 pbw of 1,2-dimethyl-quinolinium-p-toluenesulfonate and 22.2 pbw of 4-(4,6-bis-trichloromethyl-s-triazin-2-yl)-benzoylchloride in 150 ml of dried toluene. The mixture is then allowed to warm to room temperature. After 1 hour the mixture is poured onto 600 pbw of water, admixed with 600 pbw of methylene chloride and extracted by shaking. Silica gel (100 pbw) is added to the dried organic phase and the mixture is stirred for 30 minutes. The silica gel is removed by filtration and the solvents are distilled off in vacuo the residue is recrystallized from 2-methoxyethanol, giving strong red crystals.

Yield: 16.3 pbw 66.1% of theory, MP 240° C. (decomposition)

$C_{23}H_{14}Cl_6N_4O$ (575.1): calc.: C 48.03, H 2.45, N 9.74, Cl 36.99; found: C 47.9, H 2., N 9.6, Cl 36.7.

UV ($CH_2Cl_2$): λ max =460 nm.

PREPARATION EXAMPLE 6 a)
4-(biphenyl-4-yl)-3-ethyl-2-methylthiazolium-p-toluenesulfonate 4-(Biphenyl-4-yl)-2-methyl-thiazole (9.8 pbw) and ethyl p-toluenesulfonate (8.6 pbw) are stirred for 3 hours at 180° C. The hot mixture is poured onto acetone and further processed as described in Preparation Example 5(a).

b)

2-[4-(4,6-bis-trichloromethyl-s-triazin-2-yl)benzoylmethylene]-4-(biphenyl-4-yl)-3-ethylthiazoline (compound 33)

In accordance with Preparation Example 1, 5 pbw of the compound described under (a) above, 5.9 pbw of 4-(4,6-bis-trichloromethyl-s-triazin-2-yl)benzoyl-chloride and 3.5 pbw of triethylamine in 50 pbw of toluene are reacted with one another and further processed. The product is recrystallized from acetonitrile, giving red crystals.

Yield: 5 pbw 63% of theory, MP 205°-206° C. (decomposition)

$C_{30}H_{20}Cl_6N_4OS$ (697.3): calc.: C 51.68, H 2.89, N 8.03, S 4.60, Cl 30.51; found: C 51., H 3.1, N 7.8, S 4.6, Cl 29.3.

UV ($CH_2Cl_2$): λ max =430 nm.

The compounds listed in Table I below are synthesized according to the methods of preparation used in Preparation Examples 1 to 7.

The compounds are prepared as follows: Nos. 1 to 24 according to Preparation Example 1, Nos. 25 to 28 according to Preparation Example 4, Nos. 29 to 31 according to Preparation Example 3, Nos. 32 to 36 according to Preparation Example 5, Nos. 37 and 38 according to Preparation Example 2 and No. 39 according to Preparation Example 6.

TABLE I

Compounds of the general formula I

| Compound | Q | M | $R^1$ | $R^2$ | L | n |
|---|---|---|---|---|---|---|
| 1 | S | 1,2-phenylene | $CH_3$ | H | H | 0 |
| 2 | S | 1,2-phenylene | $C_2H_5$ | H | H | 0 |
| 3 | S | 1,2-phenylene | $C_3H_7$ | H | H | 0 |
| 4 | S | 1,2-phenylene | $C_4H_9$ | H | H | 0 |
| 5 | S | 1,2-phenylene | $C_5H_{11}$ | H | H | 0 |
| 6 | S | 1,2-phenylene | $C_6H_{13}$ | H | H | 0 |
| 7 | S | 1,2-phenylene | $CH(CH_3)_2$ | H | H | 0 |
| 8 | S | 1,2-phenylene | $C_6H_{11}$ | H | H | 0 |
| 9 | S | 1,2-phenylene | $CH_2C_6H_5$ | H | H | 0 |
| 10 | S | 1,2-phenylene | $C_2H_4OCH_3$ | H | H | 0 |
| 11 | S | 1,2-phenylene | $C_2H_4OC_2H_5$ | H | H | 0 |
| 12 | S | 1,2-phenylene | $C_2H_4OC_6H_5$ | H | H | 0 |
| 13 | O | 1,2-phenylene | $C_2H_5$ | H | H | 0 |
| 14 | Se | 1,2-phenylene | $CH_3$ | H | H | 0 |
| 15 | Se | 1,2-phenylene | $C_2H_5$ | H | H | 0 |
| 16 | Se | 1,2-phenylene | $C_5H_{11}$ | H | H | 0 |
| 17 | S | 1,2-naphthylene | $CH_3$ | H | H | 0 |
| 18 | S | 1,2-naphthylene | $C_5H_{11}$ | H | H | 0 |
| 19 | O | 2,3-naphthylene | $CH_3$ | H | H | 0 |
| 20 | O | 2,3-naphthylene | $C_5H_{11}$ | H | H | 0 |
| 21 | S | 3,4-tolylene | $C_2H_5$ | H | H | 0 |
| 22 | S | 4-methoxy-1,2-phenylene | $CH_3$ | H | H | 0 |
| 23 | Se | 3,4-tolylene | $CH_3$ | H | H | 0 |
| 24 | Se | 5-methoxy-1,2-phenylene | $CH_3$ | H | H | 0 |
| 25 | S | 1,2-phenylene | $C_2H_5$ | X | H | 0 |
| 26 | S | 1,2-naphthylene | $C_5H_{11}$ | X | H | 0 |
| 27 | Se | 1,2-phenylene | $C_2H_5$ | X | H | 0 |
| 28 | S | 1,2-phenylene | $C_2H_5$ | X | H | 1 |
| 29 | $C(CH_3)_2$ | 1,2-phenylene | $CH_3$ | H | H | 0 |
| 30 | $C(CH_3)_2$ | 4-chloro-1,2-phenylene | $CH_3$ | H | H | 0 |
| 31 | $C(CH_3)_2$ | 4-nitro-1,2-phenylene | $CH_3$ | H | H | 0 |

TABLE I-continued

Compounds of the general formula I

| Compound | Q | M | R¹ | R² | L | n |
|---|---|---|---|---|---|---|
| 32 | S | 1-phenyl-ethen-1,2-ylene | $C_2H_5$ | H | H | 0 |
| 33 | S | 1-biphenyl-4-yl-ethen-1,2-ylene | $C_2H_5$ | H | H | 0 |
| 34 | S | 1-tol-4-yl-ethen-1,2-ylene | $C_2H_5$ | H | H | 0 |
| 35 | S | 1-(4-methoxy-phenyl)-ethen-1,2-ylene | $C_2H_5$ | H | H | 0 |
| 36 | S | 1,2-diphenyl-ethen-1,2-ylene | $C_2H_5$ | H | H | 0 |
| 37 | S | 1,2-phenylene | $CH_3$ | H | Y | 0 |
| 38 | S | 1,2-phenylene | $C_2H_5$ | H | Y | 0 |
| 39 | —CH=CH— | 1,2-phenylene | $CH_3$ | H | H | 0 |

X = 4,6-bis-trichloromethyl-s-triazin-2-yl

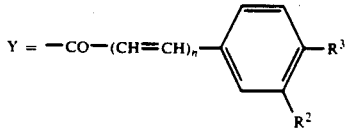

Y = —CO—(CH=CH)$_n$—⟨phenyl with R³, R²⟩

The designation of position in M has been chosen such that the radical having the lower number is attached to the nitrogen atom.

TABLE II

Compounds 1 to 39 - as far as they have not been described before - have absorption peaks at the following wavelengths (solvent $CH_2Cl_2$):

| No. | λ max (nm) |
|---|---|
| 2 | 422 |
| 3 | 425 |
| 4 | 428 |
| 5 | 428 |
| 6 | 425 |
| 7 | 426 |
| 8 | 424 |
| 9 | 429 |
| 10 | 428 |
| 11 | 428 |
| 12 | 426 |
| 13 | 400 |
| 14 | 429 |
| 15 | 430 |
| 16 | 430 |
| 17 | 448 |
| 18 | 450 |
| 19 | 390 |
| 20 | 401 |
| 21 | 429 |
| 22 | 431 |
| 23 | 432 |
| 24 | 435 |
| 26 | 388 |
| 27 | 390 |
| 28 | 416 |
| 30 | 420 |
| 31 | 427 |
| 32 | 428 |
| 34 | 432 |
| 35 | 440 |
| 36 | 430 |
| 37 | 384 |

Application Examples 1 to 10 are intended to illustrate that the photoinitiators according to the present invention, when used in photosensitive compositions to be exposed to light sources emitting in the near ultraviolet region, as are customarily used, are equal to the photoinitiators of the prior art.

APPLICATION EXAMPLE 1

An aluminum sheet electrochemically-grained and anodically-oxidized to produce an oxide layer of 2.5 g/m² is pretreated with an aqueous solution of polyvinyl phosphonic acid. The support material so prepared is coated with a solution of the following composition:

91.2 pbw of a 31% strength solution of a terpolymer of styrene, n-hexyl-methacrylate and methacrylic acid (10:60:30) having an acid number of 190, in butanone, 54.9 pbw of a 51.5% strength solution of the reaction product of 1 mole of hexamethylene diisocyanate and 2 moles of hydroxyethyl methacrylate, 2.72 pbw of compound No. 1, and 660 pbw of 2-methoxy-ethanol.

A dry-layer weight of 3.0 g/m² is obtained by spin-coating and drying for 2 minutes at 100° C. The photosensitive layer is coated with a covering layer of polyvinyl alcohol.

The printing plate obtained is exposed for 5 seconds to the light of a 5 kW metal halide lamp arranged at a distance of 110 cm under a 13-step exposure wedge containing additional line and screen elements. After exposure the plate is heated for 1 minute at 100° C. The plate is then developed with a developer of the following composition:

60 pbw of sodium metasilicate × 9H₂O 1.06 pbw of strontium chloride × 6H₂O 0.6 pbw of a non-ionic wetting agent and 2000 pbw of demineralized water.

The plate crosslinks up to step 5. The fine line and screen elements are satisfactorily rendered. After clamping onto a sheet-fed offsetprinting machine the plate readily accepts the ink supplied and produces a print run of over 100,000 prints.

APPLICATION EXAMPLE 2

A coating solution of the composition indicated below is prepared and applied to an aluminum sheet pretreated as described in Application Example 1, to give a dry layer weight of 2.8 g/m²:

102.6 pbw of a copolymer of methyl methacrylate and methacrylic acid (82:18) having an acid number of 118, added as a 34.4% strength solution in butanone, 36 pbw of trimethylolethane triacrylate, 0.7 pbw of a blue azo dye, obtained by coupling 2,4-dinitro-6-chloro-benzenediazonium salt with 2-methoxy-5-acetylamino-N-cyanoethyl-N-hydroxyethyl-aniline and 1.56 pbw of compound No. 39 in 462 pbw of 2-methoxy-ethanol.

The photosensitive layer is coated with a covering layer of polyvinyl alcohol, exposed for 30 seconds as described in Application Example 1 and developed with the developer there specified, without an additional heating operation.

A high-resolution plate is obtained, yielding almost 200,000 prints, when used on a sheet-fed offset-printing machine.

APPLICATION EXAMPLE 3

As described in Application Example 1 a photosensitive solution of the following composition is coated onto an aluminum sheet to give a dry layer weight of 3.0 g/m$^2$ and is coated with a covering layer:

32.83 pbw of a reaction product obtained by reacting a polyvinyl butyral containing 71% by weight of vinyl butyral units, 2% by weight of vinyl acetate units and 27% by weight of vinyl alcohol units with propenylsulfonyl isocyanate, having an acid number of 145 and being added as a 12% strength solution in tetrahydrofuran, 0.03 pbw of the blue azo dye indicated in Application Example 2, 3.94 pbw of the monomer described in Application Example 1, and 0.37 pbw of compound No. 29, in 87.42 pbw of 2-methoxy-ethanol.

The plate is exposed and developed as indicated in Application Example 1. A fully-crosslinked step 5 is obtained at an exposure time of 8 seconds; all screen and line elements are satisfactorily rendered. A print run of 145,000 is obtained.

APPLICATION EXAMPLE 4

A solution of 66 pbw of the terpolymer described in Application Example 1, 42 pbw of polypropylene glycol-420-dimethacrylate, 0.2 pbw of the dye specified in Application Example 2, 2.5 pbw of compound No. 15, in 240 pbw of butanone and 30 pbw of 2-methoxy-ethanol is spin-coated onto a phenoplast laminate clad with a 35 μm thick copper foil to give a layer thickness of 45 μm after drying at 100° C. The plate is exposed for 40 seconds to the light of a 5 kW metal halide lamp arranged at a distance of 110 cm from the vacuum frame. The originals used comprise a 13-step exposure wedge with density increments of 0.15 and also a line original with line widths and spaces down to 80 μm.

After exposure the layer is developed for 100 seconds with an 0.8% strength sodium carbonate solution in a spray developing apparatus. Five fully-crosslinked wedge steps are obtained.

The plate is then rinsed for 30 seconds with tap water, etched for 30 seconds in a 15% strength ammonium peroxydisulfate solution, again rinsed with water, immersed for 30 seconds into a 10% strength sulfuric acid and then electroplated successively in the following electrolyte baths:

1) 50 minutes in a copper electrolyte bath available from Schloetter, Geislingen/Steige
   Type: "Glanzkupferbad PC"
   Current density: 2.5 A/dm$^2$
   Metal deposit: approx. 25 μm
   Temperature: room temperature 2) 15 minutes in a lead-tin bath LA available from Schloetter, Geislingen/Steige
   Current density: 2 A/dm$^2$
   Metal deposit: 15 μm
   Temperature: room temperature The plate does not exhibit any undercutting or damage. The overhang or inclination, respectively, of a side wall of the resist layer is less than 10 μm for a resist width of 140 μm.

The resist stencil can be removed in a 5% strength KOH solution at 50° C. and the bared copper can then be etched away in the customary etching media.

APPLICATION EXAMPLE 5

A mechanically-grained aluminum sheet is spin-coated with a solution of:

75 pbw of a cresol/formaldehyde novolak having a melting range from 105° to 120° C., 23.8 pbw of a polyacetal of triethylene glycol and 2-butyraldehyde, 0.02 pbw of crystal violet base, and 0.6 pbw of compound No. 25, in 24 pbw of 2-methoxy-ethanol and 275 pbw of butanone and dried. The plate is exposed through an original containing a step wedge and fine line and screen elements. Development is carried out with a solution of:

5.5 pbw of sodium metasilicate × 9H$_2$O, 3.4 pbw of trisodium phosphate × 12H$_2$O, and 0.4 pbw of sodium dihydrogen phosphate in 90.7 pbw of demineralized water.

At an exposure time of 50 seconds and development after a delay of 10 minutes, 5 completely-developed wedge steps are obtained. The test elements are rendered down to the 10 μm range.

APPLICATION EXAMPLE 6

A positive dry-resist solution of the following composition was prepared:

21.2 pbw of the novolak described in Application Example 5, 10 pbw of the bis-(5-ethyl-5-butyl-1,3-dioxan-2-yl) ether of 2-ethyl-2-butyl-1,3-propanediol, 0.05 pbw of crystal violet base 3.8 pbw of polyethylacrylate of low viscosity, and 0.25 pbw of compound No. 2, in 65 pbw of butanone.

A biaxially-stretched and thermoset, 25 μm thick polyester film, pretreated with an aqueous trichloroacetic acid/polyvinyl alcohol solution, is coated with this solution. The dry layer weight is 45 g/m$^2$. This layer is laminated to both sides of a copper sheet and after cooling, peeling off the support film and postbaking in a drying cabinet at 80° C., the coated sheet is exposed on both sides with a congruent pair of originals in the form of a pocket. The exposed layer areas are developed by spray developing, using the developer solution described in Application Example 5. The plate is etched on both sides with a commercially-available ferric chloride solution until it is cleanly etched through. The resist stencils are removed with a 4% strength KOH solution and a chemically-milled component is obtained which is a perfect reproduction of the original.

APPLICATION EXAMPLE 7 AND COMPARATIVE EXAMPLES 8 TO 10

In the coating solution specified in Application Example 1 compound No. 1 is replaced by an equimolar quantity of one each of the below-indicated photoinitiators and the solutions obtained were applied to the support described in Application Example 1.

Application Example 7: Compound No. 2

Comparative Example 8: 2-(p-trichloromethylbenzoylmethylene)-3-ethylbenzothiazoline (compound No. XII of EP-A 135 348)

Comparative Example 9: 2-(4-methoxy-naphth-1-yl)-4,6-bis-trichloromethyl-s-triazine (compound No. 3 of DE-C 27 18 259)

Comparative Example 10: 2-(4-methoxy-styryl)-5-trichloromethyl-1,3,4-oxadiazole (compound No. 7 of DE-C 28 51 471)

Exposure is carried out by means of the metal halide lamp described in Application Example 1, widely used in practice, the original being covered by a gray film that increases the actual exposure time by a factor of 10.

All samples are exposed for 40 seconds and further processed as indicated in Application Example 1. The following results are obtained:

Application Example 7: 5 fully-crosslinked wedge steps,

Comparative Example 8: 4 fully-crosslinked wedge steps, step 5 partially-crosslinked, Comparative Example 9: 5 fully-crosslinked wedge steps, Comparative Example 10: 2 fully-crosslinked wedge steps, step 3 partially-crosslinked.

This shows that the photoinitiator according to the present invention, when used in the exposure to the light of commercially-available light sources emitting in the near ultraviolet region, is at least equal or even superior to the photoinitiators of the prior art.

The following Application Examples 11 to 20 are to illustrate the superiority of the photoinitiators according to the present invention, in view of their sensitivity in the visible region.

APPLICATION EXAMPLE 11 AND COMPARATIVE EXAMPLES 12 TO 15

The mixture specified in Application Example 1, in which compound No. 1 is replaced by an equimolar quantity of one of the photoinitiators indicated below, is applied to the support described in Application Example 1.

Application Example 11: Compound No. 2,

Comparative Example 12: 2-(p-trichloromethylbenzoylmethylene)-3-ethylbenzothiazoline, Comparative Example 13: 2-(4-methoxy-naphth-1-yl)-4,6-bis-trichloromethyl-s-triazine, Comparative Example 14: 2-(4-methoxy-styryl)-5-trichloromethyl-1,3,4-oxadiazole, Comparative Example 15: 2-(4-styrylphenyl)-4,6-bis-trichloromethyl-s-triazine (compound No. of EP-A 137 452)

The metal halide lamp described in Application Example 1 is used for exposure, the original being covered by a heat absorption glass filter that transmits only radiation above 400 nm.

All samples are exposed for 25 seconds and further processed as described in Application Example 1. The following results are obtained:

Application Example 11: 7 fully-crosslinked wedge steps,

Comparative Example 12: 6 fully-crosslinked wedge steps, step 7 partially-crosslinked, Comparative Example 13: 4 fully-crosslinked wedge steps, Comparative Example 14: fully-crosslinked wedge step, Comparative Example 15: 2 fully-crosslinked wedge steps.

As can be seen from the results, the photoinitiator of the present invention—besides the photoinitiator of Comparative Example 12—has its maximum activity above 400 nm.

APPLICATION EXAMPLE 16 AND COMPARATIVE EXAMPLES 17 TO 20

The mixture specified in Application Example 1, in which compound No. 1 is replaced by an equimolar quantity of one of the photoinitiators indicated below, is applied to the support described in Application Example 1.

Application Example 16: Compound No. 2,

Comparative Example 17: 2-(p-trichloromethylbenzoylmethylene)-3-ethylbenzothiazoline, Comparative Example 18: 2-(4-methoxy-naphth-1-yl)-4,6-bis-trichloromethyl-s-triazine, Comparative Example 19: 2-(4-methoxy-styryl)-5-trichloromethyl-1,3,4-oxadiazole, Comparative Example 20: 2-(4-styrylphenyl)-4,6-bis-trichloromethyl-s-triazine.

The metal halide lamp described in Application Example 1 is used for exposure, the original being covered by a heat absorption glass filter that transmits only radiation above 455 nm.

All samples are exposed for 40 seconds and further processed as described in Application Example 1. The following results are obtained:

Application Example 16: 3 fully-crosslinked wedge steps,

Comparative Example 17: 0 fully-crosslinked wedge steps,

Comparative Example 18: 0 fully-crosslinked wedge steps,

Comparative Example 19: 0 fully-crosslinked wedge steps,

Comparative Example 20: 0 fully-crosslinked wedge steps.

The results show that the photoinitiator of the present invention, under the given conditions, is the only compound capable of initiating polymerization upon exposure to radiation of wavelengths above 455 nm.

The following Application Examples are to illustrate the spectral sensitivity of photoinitiators according to the present invention and of prior art photoinitiators.

APPLICATION EXAMPLES 21 TO 31 AND COMPARATIVE EXAMPLES 32 TO 34

The mixture specified in Application Example 1, in which compound No. 1 is replaced by an equimolar quantity of one of the photoinitiators indicated below, is applied to the support described in Application Example 1.

The samples are exposed under a light source having a virtually constant emission in the range between 300 and 700 nm, through a graded light filter that is continuously transmissive between 400 and 600 nm. After development with the developer solution specified in Application Example the in-depth hardened area is determined (spectral response).

The samples are furthermore exposed through a heat absorption glass filter transmitting above 455 nm, as described in Example 16. Also in this case the developer solution described in Application Example 1 is used for development.

The table below indicates the fully-crosslinked wedge steps.

| Example | Compound No. | Spectral Response (nm) | Crosslinked Wedge Step |
| --- | --- | --- | --- |
| 21 | 1 | 430–530 | 2–3 |
| 22 | 6 | 430–530 | 2–3 |
| 23 | 10 | 430–530 | 2–3 |
| 24 | 13 | 460–480 | 1 |
| 25* | 17 | 430–570 | 4 |
| 26 | 21 | 440–540 | 5 |
| 27 | 23 | 410–580 | 9 |
| 28 | 24 | 420–580 | 10 |
| 29 | 25 | 470–520 | 2 |
| 30 | 33 | 500–550 | 3 |
| 31 | 36 | 480–550 | 4–5 |
| 32C | (1) | 415–450 | 0 |
| 33C | (2) | <400 | 0 |
| 34C | (3) | 400–420 | 0 |

*The photoinitiator can not be completely dissolved.
(1) Compound XII of EP-A 135 348
(2) Compound 1 of EP-A 137 452
(3) 9-phenylacridine In the following Application Examples 35 to 49 quantitative exposure results are recorded, which are obtained by exposure to an argon ion laser manufactured by Spectra-Physics.

APPLICATION EXAMPLES 35 TO 41

The mixture specified in Application Example 1, in which compound No. 1 is replaced by an equimolar quantity of one of the photoinitiators indicated below, is applied to the support described in Application Example 1. The samples are exposed to laser light at wavelengths of 458, 476, 488, 504 and 514 nm. Development is carried out as described in Application Example 1.

| Example No. | Compound No. | Energy Requirement (MJ/cm²) at (nm) | | | | |
| --- | --- | --- | --- | --- | --- | --- |
| | | 458 | 476 | 488 | 504 | 514 |
| 35 | 10 | 7 | 9 | 14 | 22 | 34 |
| 36 | 14 | 4 | 5 | 8 | 18 | 25 |
| 37 | 21 | 11.5 | 11 | 8 | 12 | 13 |
| 38 | 23 | 3 | 3 | 3 | 4 | 4 |
| 39 | 24 | 2 | 3 | 3 | 4 | 5 |
| 40 | 33 | 25 | 15 | 14 | 15 | 23 |
| 41 | 36 | 19 | 15 | 15 | 17 | 20 |

These examples show that the photoinitiators of the present invention respond in the visible region in accordance with practical requirements.

The following Application Examples 42 to 44 illustrate the excellent storage stability of the recording materials according to the present invention.

APPLICATION EXAMPLES 42

In accordance with Application Example 1, five photosensitive printing plates are prepared and heated at 100° C. in a circulating air oven for one, two, three and four hours, in the unexposed state. Upon termination of the respective heating times the plates are removed from the oven, cooled, exposed for 15 seconds and further processed as described in Application Example 1. For comparison, a plate not heated is exposed and processed in the same way.

The plates heated for one, two and three hours, respectively, are not practically different from the comparative sample, while the plate heated for four hours exhibits one additional crosslinked step of the continuous-tone step wedge.

This example shows the extraordinarily good thermal stability of the composition according to the present invention.

APPLICATION EXAMPLE 43

Aluminum sheets coated as described in Application Example 1 are kept, in the unexposed state, in a hotbox at a temperature of 56° C., for two, six and thirteen weeks, respectively. After the plates are removed from the hotbox they are further processed as described in Application Example 1.

Even after three months' storage in the hotbox exposed and developed plates and also the prints produced therefrom do not show any significant difference from the original plate of Application Example 1.

The plates thus have an excellent storage stability at an elevated temperature.

APPLICATION EXAMPLE 44

Aluminum sheets coated as described in Application Example 1 are kept, in the unexposed state, in a cabinet under tropical conditions, at a temperature of 42° C. and a relative humidity of 60%, for two, six and thirteen weeks, respectively. After the plates are removed from the cabinet they are further processed as described in Application Example 1.

Even after three months' storage under tropical conditions exposed and developed plates and also the prints produced therefrom do not show any significant difference from the original plate of Application Example 1.

The plates thus have an excellent storage stability under tropical conditions.

What is claimed is:

1. A compound of formula I

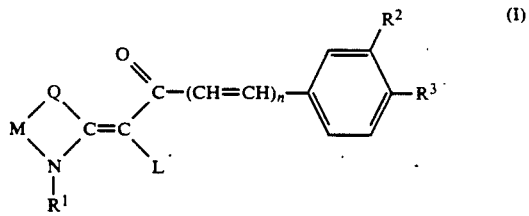

wherein
L is a hydrogen atom, a phenyl radical or a substituent of the formula

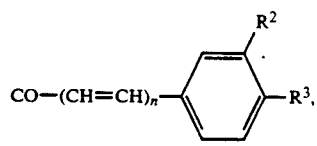

M is an alkylene radical or alkenylene radical or a 1,2-arylene radical comprising one, two or three benzene nuclei, M being unsubstituted or substituted by a member selected from the group consisting of a halogen atom, a carboxyl group, a sulfonic acid group, a nitro group, a cyano group, a carbonyl group, an alkyl group, an aryl group, an alkoxy group, a trifluoromethyl group, and an alkoxycarbonylalkyl group, Q is a sulfur, selenium or oxygen atom, a dialkyl-methylene group, an alken-1,2-ylene radical, a 1,2-phenylene radical or an N-R$^1$ group, with M+Q together forming 3 or 4 ring members, R$^1$ is an alkyl, aralkyl, aryloxyalkyl or alkoxyalkyl radical, R$^2$ and R$^3$ differ from one another and are either a hydrogen atom or a 4,6-bis-trichloromethyl-s-triazin-2-yl group, and n is 0 or 1.

2. A compound as claimed in claim 1, wherein n is 0.

3. A compound as claimed in claim 1, wherein R$^2$ is a hydrogen atom.

4. A compound as claimed in claim 1, wherein Q is a sulfur atom or selenium atom.

5. A compound as claimed in claim 1, wherein L is hydrogen.

6. A compound as claimed in claim 1, wherein M is a 1,2-phenylene radical.

7. A compound as claimed in claim 1, wherein Q is one of a sulfur atom, selenium atom, and a C(CH$_3$)$_2$ group.

8. A compound as claimed in claim 1, wherein R$^1$ is an alkyl or alkoxyalkyl radical comprising from 1 to 10 carbon atoms.

* * * * *

UNITED STATES PATENT AND TRADEMARK OFFICE
CERTIFICATE OF CORRECTION

PATENT NO. : 5,055,579

DATED : Oct. 8, 1991

INVENTOR(S) : Pawlowski et al.

It is certified that error appears in the above-identified patent and that said Letters Patent is hereby corrected as shown below:

On the title page

The title should read as follows:

[54] HETEROCYCLIC COMPOUNDS CONTAINING 4,6-BIS-TRICHLOROMETHYL-S-TRIAZIN-2-YL GROUPS

Signed and Sealed this

First Day of March, 1994

Attest:

Attesting Officer

BRUCE LEHMAN

Commissioner of Patents and Trademarks